United States Patent [19]

Sarnoff

[11] 4,004,577
[45] Jan. 25, 1977

[54] METHOD OF TREATING HEART ATTACK PATIENTS PRIOR TO THE ESTABLISHMENT OF QUALIFIED DIRECT CONTACT PERSONAL CARE

[75] Inventor: Stanley J. Sarnoff, Bethesda, Md.

[73] Assignee: Survival Technology, Inc., Bethesda, Md.

[22] Filed: July 15, 1974

[21] Appl. No.: 488,434

Related U.S. Application Data

[63] Continuation of Ser. No. 311,835, Dec. 4, 1972, abandoned, which is a continuation-in-part of Ser. No. 296,841, Oct. 12, 1972, Pat. No. 3,870,035, which is a continuation of Ser. No. 55,647, July 17, 1970.

[52] U.S. Cl. .......................................... 128/2.06 R
[51] Int. Cl.² .......................................... A61B 5/04
[58] Field of Search ................. 128/2.05 P, 2.05 R, 128/2.05 T, 2.06 A, 2.06 F, 2.06 R, 2 D, 2.1 A, 2.1 R, 213

[56] References Cited

UNITED STATES PATENTS

| 3,199,508 | 8/1965 | Roth | 128/2.06 R |
| 3,724,455 | 4/1973 | Unger | 128/2.06 A |

OTHER PUBLICATIONS

Roach, "American Journal of Medical Electronics" Jan.–Mar., 1962, pp. 51–57.

*Primary Examiner*—William E. Kamm
*Attorney, Agent, or Firm*—Cushman, Darby & Cushman

[57] ABSTRACT

A method of treating coronary prone patients when heart attack symptoms occur before qualified direct contact personal care can be administered to the patient which comprises providing each of a multiplicity of coronary prone patients with (1) a plurality of separate medicaments in self-administering form and (2) a device operable when disposed in operative relation to a patient to provide auditory signals indicative of the existing heart beat conditions of the patient, establishing communication by telephone between the patients experiencing heart attack symptoms and a source capable of making a qualified response based upon the existing heart beat conditions of the patient as to the medicament which will be effective when administered, disposing the device in operative relation with the patient and communicating the signals to the qualified source by means of the communication, communicating by means of the communication a qualified response from the source an indicated medicament which should be administered based upon the existing heart beat conditions of the patient communicated to the source and administering said indicated medicament to said patient at a time prior to qualified direct contact personal care for the patient, the qualified source preferably includes a plurality of individuals available at all times at specific telephones having medical records of the patients immediately available, including standing orders of each patient's doctor, equipment for converting the auditory signals communicated to conventional oscilloscope pictures and electrocardiograms and outgoing telephones for notifying the patient's doctor and next-of-kin and for dispatching an ambulance to the patient.

10 Claims, 6 Drawing Figures

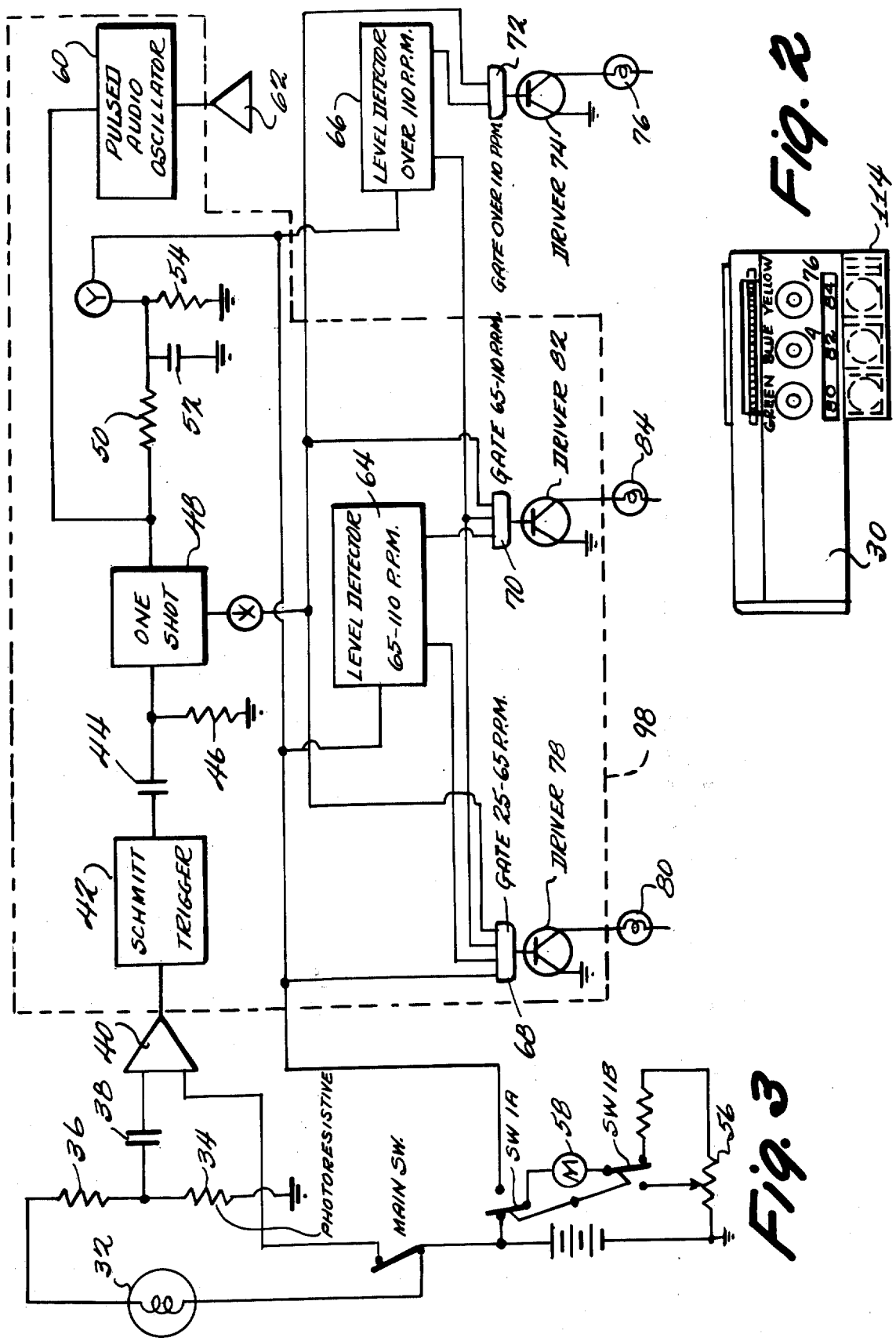

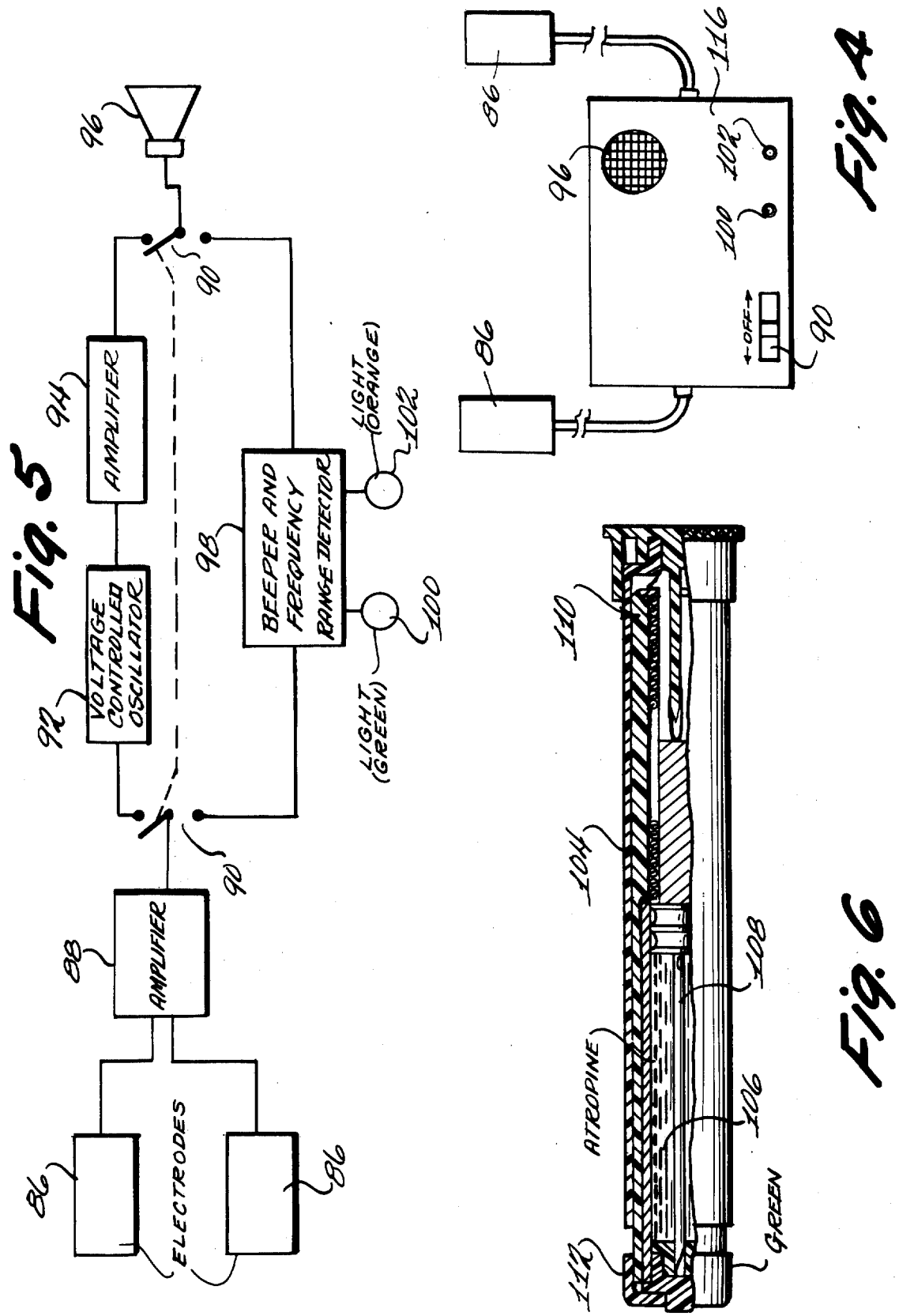

METHOD OF TREATING HEART ATTACK PATIENTS PRIOR TO THE ESTABLISHMENT OF QUALIFIED DIRECT CONTACT PERSONAL CARE

This application is a continuation of Ser. No. 311,835, filed Dec. 4, 1972, now abandoned, which in turn is a continuation in process of Ser. No. 296,841 filed Oct. 12, 1972, now U.S. Pat. No. 3,870,035, which in turn was a continuation of Ser. No. 55,647, filed July 17, 1970.

This invention relates to the treatment of individuals suspected of suffering from a coronary heart attack (acute myocardial infarction) and more particularly to improvements in the method of such treatment disclosed in my aforementioned patent which is made available to coronary prone individuals experiencing heart attack symptoms at a time prior to the establishment of qualified direct contact personal care for the individual and apparatus for use in such method.

The apparatus and method of treatment disclosed in my aforesaid patent were based upon the following considerations.

It has long been recognized that acute myocardial infarction is one of the greatest causes of death in the United States. It has also long been recognized that time is of the essence in successfully treating individuals undergoing acute myocaridal infarction. Most hospitals have established coronary care units with equipment and personnel provided for the specific purpose of administering qualified personal care directly to the patient in the shortest time possible after delivery of the patient to the hospital. Despite the operation of such coronary care units, it is estimated that in the United States more than 300,000 people who sustain acute coronary heart attacks die before they reach a hospital each year, many of them in the first hour. In an effort to treat such individuals prior to hospital delivery, mobile coronary units have been established in some high density population areas. These mobile units constitute, in essence, a hospital coronary care unit which can be brought directly to the patient so that qualified personal care can be administered as the patient is being transported to the hospital. During the course of the development of these mobile coronary care units, much of the diagnostic equipment necessary in treating myocardial infarction has been miniaturized and made more possible. Nevertheless, these mobile units are extremely costly to set up and maintain and, at best, do not provide the ultimate in time saving in that the time within which treatment can be administered is still dependent upon the time required to transport the qualified personal care into direct contact with the patient.

Thus, prior efforts to reduce the enormous death toll resulting from heart attacks have all recognized that reduction is not only dependent upon reducing the time lapse which takes place between the initial appearance of symptoms and treatment but that death reduction is almost in direct proportion to the reduction in the time lapse. The methods of time lapse reduction proposed and utilized prior to my aforesaid patent have all been directed toward minimizing the time required to effect the physical transportation between the means and personnel for administering personal care and the stricken individual, either by improved methods of rapidly transporting the victim to the personal care or the personal care to the victim. By following the principles of the invention of my aforesaid patent, the treatment of heart attack victims is, for the first time, divorced from the inherently time consuming necessity of effecting a physical transportation into direct contact between the means and personnel for administering personal care and the stricken individual. The achievement of this divorce, while relying upon the previous identification of potential heart attack victims as coronary prone and the placing of appropriate medication in the possession of such identified individuals, is much more complex than the practice heretofore known and used in identifying individuals hypersensitive to insect stings and providing such individuals with adrenalin to be self-administered immediately upon being stung if the individual exhibits signs and symptoms indicating that a hypersensitivity reaction is occurring.

With respect to the complexity of myocardial infarction treatment, it is known that ventricular fibrillation, a chaotic, uncoordinated, non-pumping contraction of the heart's ventricular muscle fibers figures prominently in producing sudden death in the prehospital phase. The mechanism which in turn precipitates ventricular fibrillation, either directly or indirectly, is generally accepted to be a ventricular ectopic beat (also called a premature ventricular contraction), an electrical impulse which arises in an abnormal or ectopic place. Such an ectopic impulse is therefore a trigger for the fatal event of ventricular fibrillation in sudden death prior to arrival in the hospital.

From the above, a key consideration in preventing a large number of coronary deaths before arrival in the hospital is the suppression of ectopic beats in the prehospital phase. Fortunately, medicaments are available which can importantly influence the incidence of ectopic beats and frequently suppress them entirely. The two most widely used medicaments at present are lidocaine and atropine. The latter medicament is also frequently helpful in correcting the varying degrees of heart block and the low blood pressure that sometimes accompanies an acute coronary heart attack. Such medicaments are in frequent use in hospitals and coronary care units for the purposes above described.

While lidocaine is generally useful in the suppression of ectopic beats, it is not advised when the heart rate is below a limit of 60 to 65 beats per minute because it has been observed that when the heart rate is below this level (bradycardia), the use of lidocaine may slow heart rate further if complete heart block is present. Atropine, on the other hand, is most useful at bradycardic rates below 60 to 65 per minute since it will elevate the heart rate, a maneuver observed to diminish or abolish the incidence of ectopic beats when bradycardia is initially present. The use of atropine when the heart rate is already quite elevated may be unwise.

In accordance with the disclosure of my aforesaid patent, treatment without the lapse of the physical transportation time factor can be achieved by placing these medicaments in self-administering form in the possession of an identified coronary prone individual (a majority of the aforesaid fatalities fall into this category) and, in addition, providing such individual with the means for immediately making a qualified determination as to which of the medicaments should be self-administered in view of his particular condition.

In my aforesaid patent, the means disclosed is in the form of a portable battery operated heart monitoring device providing means activated by the simple convenient procedure of inserting a finger in a finger-receiving structure on the device for sensing the blood pulses in the finger and rapidly and reliably producing an audible signal (in the form of a beep) for each pulse or beat of the heart. The monitoring device also included a plurality of different colored lights actuatable to indicate different heart beat frequency or rate ranges and circuitry for actuating the light corresponding with the rate of the heart beats sensed.

As disclosed in my aforesaid patent, while the device is used by the individual, the qualified determination is preferably made by a doctor or coronary care unit through instantaneous telephone communication based upon an evaluation of the existing coronary conditions of the victim (rate and rhythm) as supplied by the audible signals of the monitoring device. Under circumstances where telephone communications are not available, the device itself is used to indicate the determination by color coding the light to the medicaments provided.

In accordance with the principles of the present invention, the source is one which is at all times instantaneously available through telephone communications to the coronary prone individual. The provision of such an instantly available qualified source is important in that it makes the carrying out of the treatment procedure on a widescale basis a much more practical reality. A method of emergency treatment in which time is of the essence can only be effective when performed without delay and hence its practical utilization is dependent upon eliminating as much as is feasible every possibility of delay. Elimination of the possibility of delay due to the immediate unavailability of the victim's doctor can be practically accomplished by following the improved procedures of the present invention. These improved procedures include first, making immediately available to the source a medical history of each individual of the type that would be known to the individual's doctor; second, making immediately available to the source information as to the current ECG wave form of the individual undergoing attack symptoms; and third, making immediately available to the source, as by standing orders of the individual's doctor, the medicament determination which would be made by the individual's doctor based upon his knowledge of the individual's medical history under various different individual conditions, a particular one of which is indicated by his ECG wave form when undergoing attack symptoms.

Accordingly, it is an object of the present invention to provide an improved method of reducing the incidence of adverse cardiac conditions, such as cardiac arrhythmias, in coronary prone patients which may lead to ventricular fibrillation between the time that heart attack symptoms occur in a patient and qualified direct contact personal care can be established which embodies the principles and obtain the advantages enunciated above.

Another object of the present invention is the provision of a method of the type described employing a qualified source at all times instantly available to the coronary prone patient by telephone communication which source not only performs the step of providing the heart attack victim with a qualified response as to the proper medicament to be self-administered, but further, performs the steps of instantaneously arranging for transportation of the patient to the hospital, supplying the hospital with a medical history of the patient including conditions existing at the time of telephone communication therewith and notification of the patient's doctor and next of kin.

Another object of the present invention is the provision of a method of the type described which is simple but effective in operation.

Still another object of the present invention is the provision of apparatus of the type described which is constructed for use in such method.

These and other objects of the present invention will become more apparent during the course of the following detailed description and appended claims.

The invention may best be understood in conjunction with the accompanying drawings wherein an illustrative embodiment is shown.

In the drawings:

FIG. 2 is an elevational view of one form of apparatus embodying the principles of the present invention used in carrying out the method exemplified in FIG. 1;

FIG. 3 is a schematic wiring diagram of the portable battery-powered device shown in FIG. 2;

FIG. 4 is an elevational view of a preferred form of device;

FIG. 5 is a block diagram of the circuitry embodied in the device of FIG. 4; and FIG. 6 is an elevational view partly in section of an automatic injector forming a part of the apparatus shown in FIG. 2 and used in conjunction with the device of FIG. 4.

Figure 1:
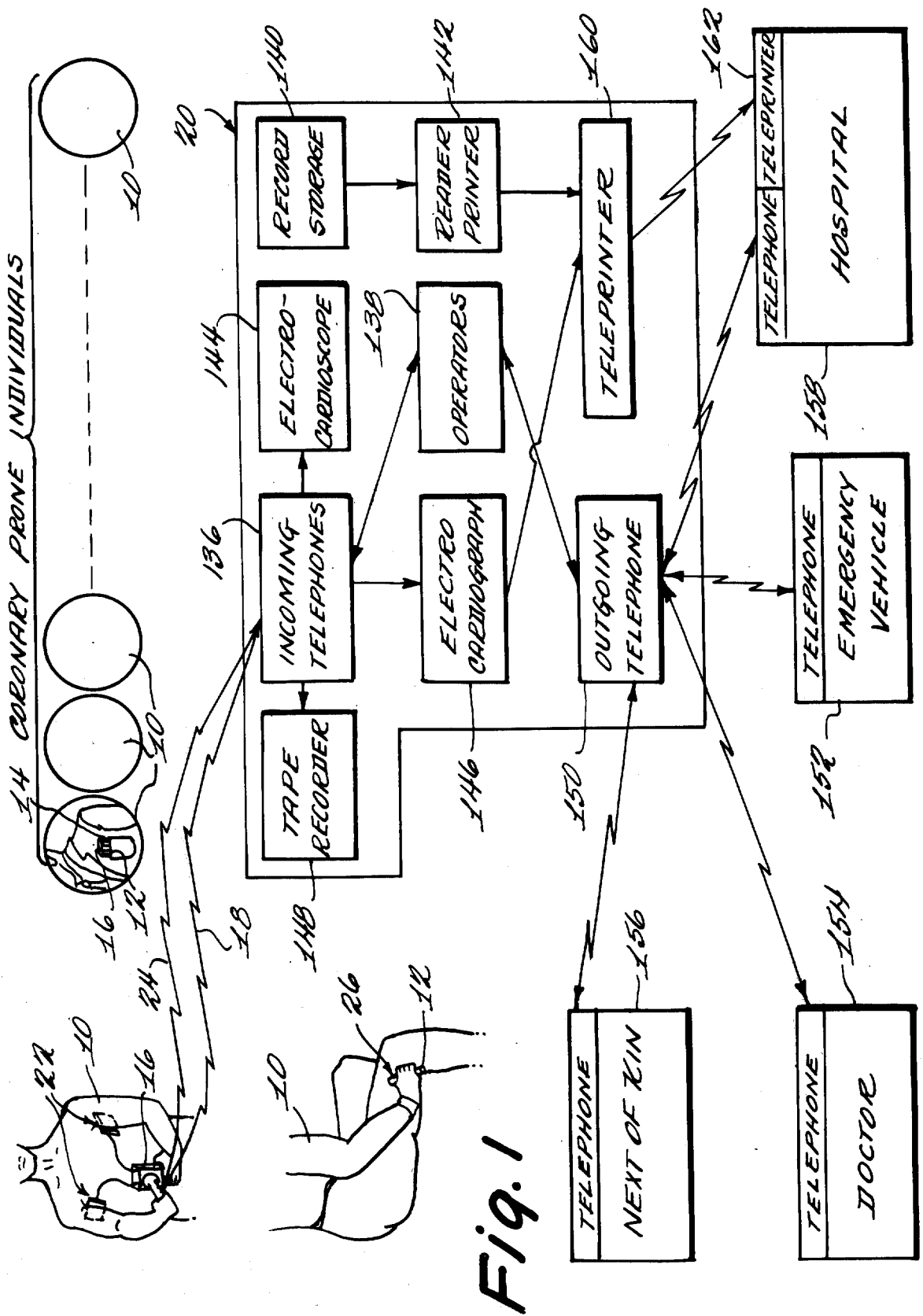
FIG. 1 is a schematic diagram exemplifying a preferred procedure for carrying out the steps of the present method.

Referring now more particularly to FIG. 1 of the drawings wherein the principles of the present invention are diagrammatically illustrated, the present method comprises the initial step of providing each of a multiplicity of coronary prone patients, schematically indicated at 10 in FIG. 1, with the following: (1) a plurality of separate medicaments, 12 and 14, in self-administering form, each of which when administered, (a) is generally effective to reduce the incidence of adverse cardiac conditions such as cardiac arrhythmias, when the existing heart beat condition is within a predetermined portion of the total range of heart beat conditions which may exist during an attack and (b) may be adversely effective when such heart beat conditions are outside the predetermined portion of the total range in which the medicament is effective as aforesaid, and (2) a device, generally indicated at 16 in FIG. 1, operable when disposed in operative relation to a patient to provide electromagnetic signals indicative of the existing heart beat conditions of the patient.

The next step in the present method occurs on the occasion of one of the aforesaid multiplicity of coronary prone patients 10 experiencing heart attack symptoms. When this occurs, the patient 10 establishes communication by telephone, as indicated at 18 in FIG. 1, with a source, generally indicated at 20 in FIG. 1, capable of making a qualified response based upon the existing heart beat conditions of the patient as to the medicament 12 or 14 which will be effective as aforesaid when administered. As soon as the telephone communication 18 has been established, the device 16 is then disposed in operative relation with the patient, as indicated at 22 in FIG. 1, and the signals thus provided by the device 16 are communicated to the qualified source 20 by means of the established telephone communication 18. Based upon the existing heart beat conditions of the patient, communicated to the source as aforesaid, the qualified source responds to the patient, as indicated at 24, through the established telephone communication indicating the medicament 12 or 14 which should be administered. Based upon the qualified response communicated to the patient, the indicated medicament 12 or 14 is immediately administered to the patient, as indicated at 26, at a time prior to the establishment of qualified direct contact personal care for the patient.

The provision of the medicaments 12 and 14 and the device 16 to each of the coronary prone patients is an essential step in the present method. These items, when combined to form apparatus in accordance with the principles of the present invention, provide the capability, when used as aforesaid, of obtaining the life saving results referred to above.

One embodiment of a combined apparatus which can be utilized in practicing the present invention is illustrated in FIG. 2. As shown, the apparatus is embodied in a common housing 30 which contains both the heart beat rate and rhythm signaling circuitry and the medicaments. This apparatus is similar to the apparatus described in detail in my aforesaid application Serial No. 55,647, the disclosure of which is hereby incorporated by reference into the present specification, but is modified and supplemented in accordance with the principles of the present invention.

Before undertaking to describe the modifications and additions, it is first appropriate to describe the circuitry as disclosed in my aforesaid patent which is schematically illustrated in FIG. 3 and includes a lamp 32 which illuminates the surface of the skin of the patient's finger when the device is disposed in operative relation to the patient. The quantity of light reflected from the skin varies in accordance with the quantity of blood present which in turn varies during each heart beat. This variation modulates a photosensitive resistor 34 which, together with resistor 36, forms a voltage divider. The AC component of the modulated voltage divider is transmitted through capacitor 38 to linear amplifier 40. The amplified output from 40 operates a Schmitt trigger 42 which gives a square wavefront whenever the preselected trigger level is exceeded.

The output from Schmitt trigger 42 is differentiated by capacitor 44 and resistor 46 to trigger a one-shot multivibrator 48. The output of the one-shot multivibrator 48 thus releases a train of impulses of equal amplitude and duration whose frequency varies as the heart beat rate. This signal is integrated in the network comprising resistor 50, capacitor 52 and resistor 54 to provide a voltage at point Y which is a function of the heart beat rate.

In order to accurately measure the heart beat rate, the voltage at point Y is compared to the voltage across a calibrated potentiometer 56 by means of a null meter 58. Thus, when the meter 58 has been nulled by varying the potentiometer 56, the calibration of the potentiometer is such that it reads in heart beats per minute. The meter 58 is also employed to check the condition of the battery power supply by means of gang switch SW1A and SW1B in conjunction with the potentiometer 56. As shown in FIG. 3, the gang switch SWIA and SWIB is in the normal operating position wherein the potentiometer 56 and null meter 58 are in series with the remainder of the circuitry across the battery power source. When it is desired to check the battery, the gang switch SWIA and SWIB moved to a position whereby the potentiometer and null meter are placed directly across the battery.

In order to provide a beep or other similar sound corresponding to the heart beat, one-shot multivibrator 48 is connected to pulsed audio oscillator 60 which is in turn connected to loud speaker 62 so that every signal from the one-shot multivibrator which respresents a single heart beat will be made audible by the oscillator and loudspeaker.

An additional determination of heart beat rate within prescribed ranges of 25–65, 65–110 and over 110 pulses per minute (ppm) is made by means of the level detectors 64 and 66 and associated circuitry. More particularly the voltage appearing at points Y which is a function of the heart beat rate is connected to level detectors 64 and 66, AND gate 68 and gang switch SW1. At the same time, the one-shot multivibrator 48 is emitting at X a train of pulses whose frequency corresponds to the heart beat rate. This signal is continuously transmitted to AND gate 72, AND gate 70, and AND gate 68.

The operation of the pulse range band circuitry is as follows. When the voltage at point Y is such that a pulse rate of over 110 is indicated, level detector 66 will be actuated to send out a signal inhibiting AND gate 70 and AND gate 68. At the same time, a pulse signal from point X is received by all three AND gates 68, 70 and 72; however, AND gates 68 and 70 have been inhibited, thus only AND gate 72 is actuated. The AND gate 72 will energize driver 74 and in turn yellow lamp 76 will be energized indicating that the heart beat rate is over 110 ppm.

When the heart beat rate is between 65 and 110 ppm only level detector 64 will be actuated. This level detector will send out a signal inhibiting AND gate 68, thus only AND gate 70 will be operative. AND gate 70 upon receiving a signal from point X and level detector 64 will actuate driver 82 and thence blue lamp 84 to indicate that the heart beat rate is between 65 and 110 ppm. Lastly, when the heart beat rate is between 25 and 65 ppm neither level detector will be energized, thus the only AND gate to be actuated upon receiving signal from point X will be 68 which in turn actuates driver 78 and green lamp 80 to indicate that the heart beat rate is between 25 and 65 ppm.

As a matter of precaution to avoid the possibility of leaving the main switch on and perhaps depleting the battery power supply, the main switch has been incorporated in the sensing unit. Thus when the finger is placed in the sensing unit the main switch is operated to place the circuit in operative condition.

A device 16 embodying the above described circuitry and mode of operation is advantageous because of its simplicity. By sensing the circulatory blood pulses in the finger, a minimum inconvenience is imposed upon the patient. By converting each pulse to a well-defined auditory signal or "beep" a clear indication of the existing heart beat rate and rhythm of the patient is provided which is capable of transmission over the established telephone communication in conventional fashion. Finally, by detecting the existing heart beat rate and selectively energizing one of a plurality of lights, each of which indicates a particular heart beat rate range, there is provided an instantaneous indication pertinent to the qualified response as to the proper medicament to be administered. Thus, in practicing the present invention it may be desirable for the patient to verbally communicate over the established communication, the color of the light which is being energized at each heart beat. Moreover, by color coding the medicaments in corresponding fashion to the lights, there is provided the capability of the patient utilizing the lighted color as a response to administer the correspondingly colored medicament in dire emergency situations where it is impossible or impractical to establish any telephone communication whatsoever.

It can thus be seen that a device 16 embodying the circuitry described above is operable when disposed in operative relation to a patient to provide electromagnetic signals indicative of the existing heart beat conditions of the patient. The electromagnetic signals provided are preferably within the auditory range since such signals are capable of direct transmission over conventional telephone circuits. Other signals capable of such transmission may be utilized which are either capable of telephone transmission by direct hook-up or by an appropriate conversion.

A disadvantage of the utilization of pulse sensing devices (whether sensed at the finger or other locations) is that they do not provide the capability of producing an electrocardiogram and the indications inherent therein which materially aid in formulating the response by the source 20. Accordingly, in practicing the principles of the present invention a device 16 is utilized having circuitry which senses the electrical impulses of the heart and translates these impulses into electrical signals capable of transmission over the established telephone communication so that they can be converted into an ECG wave form. Such circuitry is known per se and one example thereof is disclosed in the U.S. patent to Tygart No. 3,426,150, the disclosure of which is hereby incorporated by reference into the present specification.

A particularly critical problem encountered in utilizing circuitry of this type is the reliability and simplicity of the electrodes used to pick up or sense the electrical impulses of the heart. What is needed is a sensing means which can be disposed in operative relation with the patient without the necessity of initially applying conductive pastes or the like to the patient's skin or elaborate means to maintain the electrodes in operative relation and still obtain a reliable sensing without excess artifact. A preferred sensing means which meets this criteria is disclosed in co-pending commonly assigned application Ser. No. 230,753, filed Mar. 1, 1972 which issued Feb. 19, 1974, as U.S. Pat. No. 3,792,700, the disclosure of which is hereby incorporated by reference into the present application.

In FIG. 4, there is disclosed a preferred device 16 which utilizes the sensing means of the aforesaid application and a circuit, shown schematically in block diagram in FIG. 5, which utilizes the beeper and frequency range light features advantageously employed in the circuit of FIG. 3, together with the further advantageous feature of electrocardiogram production, as with the Tygart circuit.

As best shown in FIG. 5, the circuit includes a pair of electrodes 86, constructed and operated in accordance with the disclosure of the aforesaid application Ser. No. 230,753. The relatively feeble voltages in the order of one millivolt or more, developed by the heart and picked up by the electrodes 86 are sent to an amplifier 88, the output of which is then conducted to a selector switch 90 of the three position type, the central position being an off power position. In one extreme position of the switch 90, the output of the amplifier 88 is conducted to a voltage controlled oscillator 92. The oscillator 92 (corresponding to Tygart's oscillator 13) is selected so that when no input voltage is present to be amplified by amplifier 88, the oscillator operates at a frequency within the range of audibility and preferably within that range of frequencies for which communications links used primarily for speech transmission are designed. The operating frequency of oscillator 92 is deviated from its normal value when a signal from amplifier 88 is applied thereto, so that the instantaneous frequency of the oscillator is a function of the voltage amplitude measured by the electrodes 86 applied under the armpits of the patient's body and thus, is a function of the operation of the heart.

The output of oscillator 92 is passed to an amplifier 94 and is then supplied to an electro-acoustic transducer or loudspeaker 96 under the control of switch 90.

When switch 90 is in its other extreme position, the output of the amplifier 88 is fed to a beeper and frequency range detector circuit 98 which includes the elements of the circuit of FIG. 3 enclosed within the broken line and indicated at 98.

In the preferred embodiment, only two frequency range lights (green) 100 and (orange) 102 are utilized and the single level detector (64) utilized is preferably set at 60 ppm and above. For purposes of the present method, the ECG circuit will normally be utilized, although the beeper and frequency range detector circuit and lights may be used in emergency situations, as aforesaid. Moreover, it will be understood that the ECG circuit may be expanded to include the calibration pulse generator and muting components of the Tygart circuit, if desired.

Where only two frequency ranges are utilized, as set forth above, the medicaments 12 and 14 are preferably atropine and lidocaine. Insofar as the self-administering form of the medicaments is concerned, they may be in any of the well-known self-administering forms appropriate for the particular medicament involved. In the specific examples of both lidocaine and atropine, the medicaments are in liquid form and are appropriately administered in such form by hypodermic injection. A preferred form of self-administration is to provide an appropriate dosage within an automatic injector of the type such as described in U.S. Pat. No. 2,832,339, the disclosure of which is hereby incorporated by reference into the present specification. It has been found in recent studies that injections of liquid medicaments with devices of this type into muscle tissue have a dispersion rate superior to that of a conventional hypodermic syringe when injected into muscle tissue. Moreover, while the present invention contemplates the utilization of conventional syringes for intravenous injection, the use of self-injecting devices of the type indicated above is preferable because of the simpler procedure involved in effecting self-administration as compared with conventional syringes particularly when administered intravenously.

An automatic injector is shown in detail in FIG. 5, the construction and operation of which will be apparent by reference to the aforesaid U.S. Pat. No. 2,832,339. For present purposes, it is sufficient to note that the automatic injector includes a housing 104 within which is contained an appropriate dosage of liquid medicament 106, such as atropine, a hypodermic needle 108 and means 110 for simultaneously effecting (1) a rapid movement of the needle 108 outwardly of the housing 104 into the muscle tissue of a patient and (2) a rapid movement of the liquid medicament 106 outwardly through the needle.

The movement effecting means 110 may take many forms and operate in any known fashion. In the preferred embodiement shown, operation is accomplished by the patient gripping the housing 104 and pushing a cap element 112 into an appropriate portion of the body having sufficient muscle tissue to receive the medicament, as for example, the thigh, as shown at 26 in FIG. 1.

The injector as shown is advantageous for several reasons, among which is the fact that the medicament can be safely stored therein for an extended period of time in a form which can be readily handled. Likewise, the needle is protected at all times and completely unexposed to the user until after injection has been accomplished. The operation is initiated by a simple act on the part of the patient and takes place so rapidly that injection of the medicament occurs, with the superior dispersion effect as aforesaid, without any anticipatory dread, as with an exposed needle. Moreover, injection can be accomplished through clothing, if necessary.

Color coding of the medicament when contained within a self-injector is best accomplished by providing the appropriate color on the exterior of the injector, such as the housing 104 or end cap or both. In the case of the preferred apparatus, the injector containing atropine, as shown in FIG. 6, includes green coloring on the exterior thereof. A preferred manner of coloring would be to form the end cap 112 and/or housing of plastic material molded with a green coloring agent therein. The green coloring for the atropine injector is coded with the green light 100 which is energized by a heart beat at a rate below 60 pulses per minute. A similar injector containing lidocaine as the medicament and colored orange is coded to the orange light 102 which is energized by a heart beat at a rate above 60 pulses per minute.

With reference to FIG. 2, the apparatus of the present invention is contained within the common housing or casing 30, which is provided with a three compartmented receptacle 114 secured directly beneath the color coded lights 80, 84 and 76. Each compartment is provided with a medicament in a self-injector color coded to correspond to its compartment which is in turn color coded to correspond to the lights 80, 84 and 76. In this embodiment light 80 is shown as being colored green and the associated compartment and self-injector colored correspondingly green contains atropine, or the like, for use with a heart beat range of up to 65 ppm. The light 84 is colored blue and the associated compartment and self-injector colored correspondingly blue contains lidocaine, or the like, for use with a heart beat range of 65 to 110 ppm. The light 76 is colored yellow and the associated compartment and self-injector colored correspondingly yellow contains practalol, or the like, for use with a heart beat range of about 110 ppm.

With reference now to FIG. 4, the preferred device 16 is shown within a housing 116 separate from the auto-injectors containing the medicaments 12 and 14. The housing 116 is of a size to easily fit within the breast pocket of a shirt or jacket and may be provided with conventional clips (not shown) for retention therein. Each auto-injector may likewise be provided with such clips (not shown) for storage within the pocket alongside the device 16 as clearly indicated in FIG. 1. With the pocket size device 16, the loudspeaker 96 is fixed within the housing 116, as shown in FIG. 4, and when the signals emitted therefrom are to be transmitted over the established telephone communication, the telephone receiver is simply held in a position adjacent the loudspeaker 96, as shown in FIG. 1. It will be understood, however, that a reel mounted loudspeaker may be utilized, as disclosed in my co-pending application.

In addition to the above, it is within the contemplation of the present invention to provide each coronary prone patient 10 with an additional device (not shown) operable to measure and determine the patient's blood pressure. Conventional devices of this type may be provided as well as miniaturized devices of the type such as that disclosed in U.S. Pat. No. 3,103,214 dated Sept. 10, 1963. It will be understood, however, that the provision of blood pressure indicating devices, while desirable, is not essential to the practice of the present invention.

As previously indicated, the qualified source 20 may be simply the patient's doctor utilizing whatever telephone communication is utilized by him. However, it is preferable in accordance with the principles of the present invention that the source be one which is at all times instantaneously available through a specific telephone communication. Such instantaneous and continuous availability is best provided in accordance with the principles of the present invention by providing a plurality of telephones, preferably of the type operable to automatically sequence to the next number in the event that the original number is not open. Preferably, the plurality of incoming telephones, indicated at 136 in FIG. 1, are disposed at a single qualified source station, indicated in the drawing by the block designated the source 20. The source 20 also includes sufficient personnel, indicated at 138, at the station at all times, 24 hours a day, available to establish the telephone communications 18 and 24 in the conventional fashion. The preferred source 20 also includes a patient record storage, generally indicated at 140, which contains information concerning each of the patients 10 including name, address, and telephone number, a medical history including such data as birth date, sex, etiology, anatomy, physiology, functional class, therapeutic class, blood pressure, and other pertinent medical data. The records also preferably include a listing of the patient's doctor, together with telephone numbers by which the doctor can be reached, a hospital where the patient would be treated in the event of a heart attack, and the telephone number of the hospital, an ambulance telephone number appropriate for the designated hospital, a designation of next-of-kin and the relationship with the patient, as well as the telephone number thereof, an indication of what current therapy the patient is undergoing and any drug allergies which the patient may have, plus standing orders of the patient's doctor as to which of the two medicaments 12 and 14 in the possession of the patient should be indicated to be administered, based upon the existing heart beat conditions of the patient. Finally, the records of the patient might include the most recent electrocardiogram with an indication of the date thereof.

The records may be stored in any fashion, one preferred mode of storage is to convert the written record to a microfilm image and to collect the microfilm images in a device capable of rapid retrieval at the source station. A specific example of such a device is the Mohawk Data Retriever. Where a device of this type is used, a microfilm reader-printer, generally indicated at 142 in FIG. 1, is also provided in order to permit the operator 138 at the source station to obtain a visual reading of the record. It will be understood that other types of record storage and retrieval may be utilized, including computer storage at remote locations with a read-out or printer at the source station.

The preferred source 20 also includes at the station a demodulating device (not shown) which is connectable with the telephone receiver for converting the audible signals, communicated thereto from the loud speaker 96 through the communication 18, into electrical signals of the type which will operate a conventional oscilloscope or electrocardioscope, indicated at 144 in FIG. 1. A specific example of a device of this type is produced under the trade name Physiocontrol Monitor (with cardiotachometer). In addition, a demodulator device (not shown) is provided capable of converting the communicated signals into corresponding electrical voltage signals which are fed to a conventional electrocardiograph machine indicated at 146 in FIG. 1, as for example, a Cambridge Transrite 4-2. In regard to the demodulating devices, see Tygart Pat. No. 3,426,151, the disclosure of which is hereby incorporated by reference into the present specification. Optionally, a conventional tape recorder, indicated at 148 in FIG. 1 as for example a Phillips Pro 12, is likewise connected to the input telephone 136, for the purpose of recording the entire telephone communication 18 and 24.

It can be seen that the operator 138 at the source station by viewing the oscilloscope 144 and the records of the particular patient on the reader 142 and specifically the doctor's standing orders indicated thereon, can then provide the patient with a qualified response over the telephone communication 24 as to which of the plurality of medicaments 12 and 14 should be administered to the patient. It will be apparent, that the actual administering of the medicament to the patient, as shown at 26 in the drawings, can be performed by other individuals in the presence of the patient, as well as the patient himself.

In accordance with the principles of the present invention, it is preferable that the operators 138 of the source 20 also perform additional procedural steps which will materially aid in the continuing treatment of the patient after the administering of the indicated medicament has been accomplished. To this end, the plurality of telephones at the source station include one or more outgoing telephones, indicated at 150 in FIG. 1, by which an operator 138 at the station can establish communications with the operator of an ambulance or other emergency vehicle, such as a helicoptor or the like, as indicated at 152 in FIG. 1, so that such emergency vehicle will be dispatched to the patient as soon as possible for transportation to the designated hospital. Likewise, the outgoing telephones 150 are used by the operators 138 to notify the patient's doctor, as indicated at 154 in FIG. 1, and the patient's next-of-kin, as indicated at 156 in FIG. 1, all of which are indicated on the records as aforesaid. In addition, in order to eliminate any delay at the hospital, the telephones 150 may be used by the operators 138 to communicate with the hospital, as indicated at 158 in FIG. 1, whatever entrance information is required by the hospital, such information likewise being indicated on the records. Also, it is preferable in accordance with the principles of the present invention to provide both at the source station and at the hospital conventional teleprinting devices (eg telecopier) indicated at 160 and 162 in FIG. 1, which enable the operator to instantly transmit to the hospital both the patient's record as well as the electrocardiogram obtained from the electrocardiograph 146 during the communications 18 and 24 with the patient.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. A method of participating in the pre-hospital phase treatment of coronary prone individuals by any one of said individuals and/or non-qualified persons in direct contact therewith at a time during the early minutes or hours after the onset of heart attack symptoms, each of which individuals has been previously provided with (1) a plurality of separate injectors suitable for self-administration under the disconcerting circumstances present during the aforesaid time, each containing a liquid dosage of a different medicament non-intravenously injectable into the individual effecting the self-administration of the injector, each of which medicaments (a) when so injected is generally effective to reduce the incidence of adverse cardiac conditions, such as ectopic beats, when the existing heart beat condition is within a different predetermined portion of the total range of heart beat conditions which may exist during an attack, and (b) may be inadvisable or unwise to inject when such heart beat conditions are outside the predetermined portion of the total range in which the medicament is effective as aforesaid, and (2) a diagnosing device having electrode means operable to be simply and conveniently disposed in operative relation to an individual for sensing the electrical impulses which trigger the heart beat and battery operated signal producing means operable when said electrode means is disposed in said operative relation to produce ECG signals indicative of the sensed heart beat conditions of the individual, said method comprising the steps of:

1. maintaining in a readily accessible and producible form medical history information of each of said individuals including standing orders by each individual's doctor as to an indicated medicament to be administered based upon an indicated range portion of the heart beat conditions of the individual existing at the time of an attack,
2. establishing at a central station communication by telephone with any one of said individuals experiencing heart attack symptoms,
3. receiving at said central station over the established telephone communication information as to the identity of the individual experiencing heart attack symptoms,
4. obtaining access to the maintained medical history information including said standing orders applicable to the identified individual,
5. producing the medical history information of the identified individual including the standing orders applicable thereto for utilization in formulating a qualified response, 6. receiving ECG signals over the established telephone communication which are (a) produced by the signal producing means of the device with said electrode means in operative relation to the individual experiencing heart attack symptoms and (b) transmitted over the established telephone communication, 7. producing the received ECG signals for utilization in formulating a qualified response, 8. utilizing the produced medical history information including said standing orders and the produced ECG signals to formulate a qualified response at the central station, such as would be arrived at by the individual's doctor, based upon the standing orders of the individual's doctor, and 9. transmitting from the central station over the established telephone communication the aforesaid qualified response.

2. A method as defined in claim 1 wherein said medical history record of each individual includes a previously recorded ECG wave form of the individual and the date of recording thereof, said method further including the steps of communicating information from said central station appropriate to effect the rapid dispatch of an emergency vehicle to the vicinity of said individual to transport said individual to a hospital, transmitting from said central station to said hospital by electromagnetic waves the medical history of said individual including said previously recorded ECG wave form and the produced ECG signals for use when said individual arrives at said hospital in the emergency vehicle dispatched.

3. A method as defined in claim 2 wherein said medical history records of each individual including said previously recorded ECG wave form are maintained in microfilm image form and wherein the production of said medical history records comprises projecting said microfilm image in enlarged form on a first screen, the production of said ECG signals comprising temporarily producing the same as a wave form on a second screen.

4. A method as defined in claim 3 wherein the production of said ECG signals also includes simultaneously producing the same as a line wave form on sheet material and the production of the medical history records of said individual also includes converting the microfilm image form thereof at said central station into an enlarged line form on sheet material, said transmitting of the medical history and ECG signals from said central station to said hospital comprising operating a teleprinting device utilizing the ECG signals in line wave form on sheet material and the medical history records in line form on sheet material as an input thereto to effect said transmittal.

5. A method as defined in claim 4 including the step of continuously recording at said central station the established telephone communication with said individual.

6. Apparatus for use in participating in the prehospital phase treatment of coronary prone individuals by any one of said individuals and/or non-qualified persons in direct contact therewith at a time during the early minutes or hours after the onset of heart attack symptoms, each of which individuals has been previously provided with (1) a plurality of separate injectors suitable for self-administration under the disconcerting circumstances present during the aforesaid time, each containing a liquid dosage of a different medicament non-intravenously injectable into the individual effecting the self-administration of the injector, each of which medicaments (a) when so injected is generally effective to reduce the incidence of adverse cardiac conditions, such as ectopic beats, when the existing heart beat condition is within a different predetermined portion of the total range of heart beat conditions which may exist during an attack, and (b) may be inadvisable or unwise to inject when such heart beat conditions are outside the predetermined portion of the total range in which the medicament is effective as aforesaid, and (2) a diagnosing device having electrode means operable to be simply and conveniently disposed in operative relation to an individual for sensing the electrical impulses which trigger the heart beat and battery operated signal producing means operable when said electrode means is disposed in said operative relation to produce ECG signals indicative of the sensed heart beat conditions of the individual, said apparatus comprising: a central station, means for maintaining in a readily accessible and producible form medical history information of each of said individuals including standing orders by each individual's doctor as to an indicated medicament to be administered based upon an indicated range portion of the heart beat conditions of the individual existing at the time of an attack, means at said central station for establishing communication by telephone with any one of said individuals experiencing heart attack symptoms over which information as to the identity of said individual experiencing heart attack symptoms can be received, means for obtaining access to the maintained medical history information including said standing orders applicable to the identified individual, means for producing the medical history information of the identified individual including said standing orders for utilization in formulating a qualified response, means for receiving over the established telephone communication signals capable of production in ECG form representative of the electrical impulses which trigger the heart beat transmitted over the established telephone communication through the operation of said device with the electrode means in operative relation with the individual experiencing heart attack symptoms, and means for producing the ECG signals for utilization with the produced medical history information including said standing orders to formulate a qualified response, such as would be arrived at by the individual's doctor, based upon the standing orders of the individual's doctor, which qualified response is transmitted from the central station over the established telephone communication.

7. Apparatus as defined in claim 6 wherein said medical history record of each individual includes a previously recorded ECG wave form of the individual and the date of recording thereof, said apparatus further including means for communicating information from said central station appropriate to effect the rapid dispatch of an emergency vehicle to the vicinity of said individual to transport said individual to a hospital and means for transmitting from said central station to said hospital by electromagnetic waves the medical history of said individual including said previously recorded ECG wave form and the produced ECG signals for use when said individual arrives at said hospital in the emergency vehicle dispatched.

8. Apparatus as defined in claim 7 wherein said means for maintaining said medical history records of each individual including said previously recorded ECG wave form include means for maintaining the same in microfilm image form, said means for producing said medical history includes means for projecting said microfilm image in enlarged form and first screen means for receiving said projected image, said ECG producing means includes an electrocardioscope.

9. Apparatus as defined in claim 8 wherein said ECG signals producing means also includes an electrocardiograph, said medical history producing means also includes means for producing on sheet material an enlarged line form of the microfilm image, said electromagnetic wave transmitting means comprising a teleprinting device.

10. Apparatus as defined in claim 6 including means at said central section for continuously recording the established telephone communication with said individual.

* * * * *